United States Patent
Xu et al.

(10) Patent No.: US 11,834,481 B1
(45) Date of Patent: Dec. 5, 2023

(54) SALTY TASTE ENHANCING PEPTIDE DERIVED FROM DRY-CURED HAM AND PREPARATION METHOD THEREOF

(71) Applicants: Hefei University of Technology, Hefei (CN); Yunnan Agricultural University, Kunming (CN)

(72) Inventors: Feiran Xu, Hefei (CN); Baocai Xu, Hefei (CN); Xuefeng Wang, Hefei (CN); Zhaoming Wang, Hefei (CN); Bao Zhang, Hefei (CN); Fei Ma, Hefei (CN); Ying Wu, Hefei (CN); Kai Zhou, Hefei (CN); Hui Zhou, Hefei (CN); Kezhou Cai, Hefei (CN)

(73) Assignees: Hefei University of Technology, Hefei (CN); Yunnan Agricultural University, Kunming (CN)

( * ) Notice: Subject to any disclaimer, the term of this patent is extended or adjusted under 35 U.S.C. 154(b) by 0 days.

(21) Appl. No.: 18/327,086

(22) Filed: Jun. 1, 2023

(30) Foreign Application Priority Data

Jun. 30, 2022 (CN) .......................... 202210756898.X

(51) Int. Cl.
| | |
|---|---|
| *C07K 7/06* | (2006.01) |
| *A23J 1/02* | (2006.01) |
| *A23L 13/30* | (2016.01) |
| *A23L 27/40* | (2016.01) |
| *A23L 33/18* | (2016.01) |
| *C07K 14/47* | (2006.01) |
| *C07K 1/18* | (2006.01) |
| *C07K 1/14* | (2006.01) |

(52) U.S. Cl.
CPC ................ *C07K 14/47* (2013.01); *A23J 1/02* (2013.01); *A23L 13/30* (2016.08); *A23L 27/45* (2016.08); *A23L 33/18* (2016.08); *C07K 1/145* (2013.01); *C07K 1/18* (2013.01); *C07K 7/06* (2013.01)

(58) Field of Classification Search
CPC . C07K 1/145; C07K 1/18; C07K 1/36; C07K 5/06113; C07K 7/06; A23J 1/02; A23J 3/04; A23L 13/30; A23L 27/45; A23L 33/18
See application file for complete search history.

(56) References Cited

U.S. PATENT DOCUMENTS

| | | | |
|---|---|---|---|
| 11,072,644 B2 * | 7/2021 | Rajpal .............. | C07K 14/70578 |
| 2004/0031072 A1 * | 2/2004 | La Rosa ................ | C07H 21/04 |
| | | | 536/23.6 |

FOREIGN PATENT DOCUMENTS

CN          115028682 A  *  9/2022  ............. C07K 5/072

OTHER PUBLICATIONS

Khodorova et aol. Consumption of Boiled, but Not Grilled, Roasted, or Barbecued Beef Modifies the Urinary Metabolite Profiles in Rats. Molecular Nutrition and Food Research. Published online May 6, 2022, vol. 66, No. 2100872 , ten pages. (Year: 2022).*
Liao et al. LC-MS/MS-based metabolomics and sensory evaluation characterize metabolites and texture of normal and spoiled dry-cured hams. Food Chemistry. Available online Sep. 17, 2021, vol. 371, No. 131156. (Year: 2022).*

* cited by examiner

*Primary Examiner* — Jeffrey E. Russel
(74) *Attorney, Agent, or Firm* — Porus IP LLC

(57) ABSTRACT

A salty taste enhancing peptide derived from dry-cured ham is provided, and the amino acid sequences thereof are Asp-Leu; Phe-Met-Ser-Ala-Leu-Phe, as shown in SEQ ID NO: 1; and His-Val-Arg-Arg-Lys, as shown in SEQ ID NO: 2. The salty taste enhancing peptide in the present disclosure is of small molecular weight, features easy separation and purification, has strong salty taste enhancing effect and simple sequences, and is easy to synthesize, therefore, the salty taste enhancing peptide can be applied to the fields of food, health products, medicine and biology, and is expected to replace salt substitute products currently available on the market.

7 Claims, 6 Drawing Sheets

Specification includes a Sequence Listing.

| Sephadex G-15 components | TD | Flavor description |
|---|---|---|
| Component DHH-G1 | 8 | General salty taste enhancing effect |
| Component DHH-G2 | 16 | Obvious salty taste enhancing effect |
| Component DHH-G3 | 0 | No salty taste enhancing effect |
| Component DHH-G4 | 5 | Weak salty taste enhancing effect |

| Ion-column purified components | TD | Flavor description |
|---|---|---|
| Component DHH-G2-E1 | 32 | Strong salty taste enhancing effect |
| Component DHH-G2-E2 | 34 | Obvious salty taste enhancing effect |
| Component DHH-G2-E3 | 0 | No salty taste enhancing effect |

SALTY TASTE ENHANCING PEPTIDE DERIVED FROM DRY-CURED HAM AND PREPARATION METHOD THEREOF

CROSS REFERENCE TO THE RELATED APPLICATION

This application is based upon and claims priority to Chinese Patent Application No. 202210756898.X, filed on Jun. 30, 2022, the entire content of which is incorporated herein by reference.

SEQUENCE LISTING

The instant application contains a Sequence Listing which has been submitted in XML format via EFS-Web and is hereby incorporated by reference in its entirety. Said XML copy is named GBTXD002_Sequence_Listing.xml, created on 05/29/2023, and is 3,392 bytes in size.

TECHNICAL FIELD

The present disclosure belongs to the field of biotechnology, and relates to a salty taste enhancing peptide derived from dry-cured ham and a preparation method thereof.

BACKGROUND

At present, salty taste in food is still mainly from edible salt (main component is NaCl). However, it is reported that each Chinese person typically consumes more than 10 g of salt per day, and excessive intake of salt may impair homeostasis and blood pressure stability, and induce hypertension, stroke and other cardiovascular diseases. Increasing the salty taste without increasing sodium content in salt, and achieving salt reduction without reducing salty taste have always been research hotspots.

Salty taste enhancing peptides can significantly increase salty taste without increasing the content of salt. Taste is an important factor for measuring food quality. Peptides extracted from food proteins are also dietary components that may affect the taste of food, so they may be valuable ingredients when considering regulating the taste of food and using them as salty taste enhancers. This type of salty taste enhancing peptides can be recommended to be a healthy food suitable for preventing civilized diseases such as obesity or cardiovascular diseases.

Premium ham products contain a variety of polypeptide substances, amino acid molecules and the like, and are closely associated with small molecular substances, including amino acids, polypeptides and the like, particularly small molecular polypeptides, which may have a strong effect of enhancing the salty taste, that is, salty taste enhancing peptides.

Therefore, a salty taste enhancing peptide derived from dry-cured ham with a clear structure and significant salty taste enhancing effect, and a preparation method thereof, which are developed by taking ham as a source through separation, purification and identification technology and sensory characteristic analysis have very great market value and application value.

SUMMARY

An objective of the present disclosure is to provide a dry-cured ham-derived polypeptide capable of alleviating alcoholic liver injury and a preparation method thereof.

In order to achieve the above and other related objectives, the present disclosure provides technical solutions as follows: a salty taste enhancing peptide derived from dry-cured ham, where the amino acid sequences thereof are: Asp-Leu; Phe-Met-Ser-Ala-Leu-Phe, as shown in SEQ ID NO: 1; or His-Val-Arg-Arg-Lys, as shown in SEQ ID NO: 2.

A preferred technical solution is: the amino acid sequences thereof are: Asp-Leu.

In order to achieve the above objective and other related objectives, the present disclosure provides technical solutions as follows: a preparation method of a salty taste enhancing peptide derived from dry-cured ham, including the following steps:

S1. Preparation of Ham-Derived Extract

Processing the ham to obtain power, dispersing the power in a hydrochloric acid buffer solution, homogenizing and then centrifuging the powder, taking the supernatant and performing suction filtration, and obtaining ham-derived extract after suction filtration;

S2. Dialysis and Preparation of the Ham-Derived Extract

Dialyzing the ham-derived extract to obtain dialysate, concentrating the dialysate to obtain a concentrated solution, freezing and drying the concentrated solution to obtain crude polypeptides.

S3. Separation and Purification of the Crude Polypeptides

Dissolving the crude polypeptides in pure water, loading the filtered solution onto a Sephadex G-15 gel filtration column for purification, obtaining purified peptides, performing further purification by ion exchange chromatography, carrying out a sensory evaluation on all purified components according to their respective chromatographic peaks, and screening out components with the optimal salty taste enhancing effect through the sensory evaluation and analysis of electronic tongue-assisted sensory characteristics.

S4. Amino Acid Sequence Test of the Salty Taste Enhancing Peptide

Performing an ultra-high-performance liquid chromatography-triple quadrupole time-of-flight mass spectrum ("UPLC-Triple-TOF/MS" for short) on components with the optimal salty taste enhancing effect obtained in S3 to identify sequences of the salty taste enhancing peptide, and determining three amino acid sequences as Asp-Leu; Phe-Met-Ser-Ala-Leu-Phe, as shown in SEQ ID NO: 1; and His-Val-Arg-Arg-Lys, as shown in SEQ ID NO: 2.

A preferred technical solution is as follows: in S1, the concentration of the hydrochloric acid buffer solution is 0.01 mol/L, and the ratio of the powder to the hydrochloric acid buffer solution is 50 g: 100-200 mL; homogenate is performed 3-5 times at 15,000-18,000 r/min for 8-12 s each time; centrifugation is performed at a rotating speed of 10,000-14,000 r/min at −3--−5° C. for 15-25 min; and the supernatant is subject to suction filtration with a 0.45 μm filter membrane.

A preferred technical solution is as follows: in S2, the ham-derived extract is placed into a dialysis bag of less than 3,000 Da and dialyzed for 20-28 h at −3--−5° C., and the obtained dialysate is evaporated by rotary steaming at 60-70° C. to obtain a concentrated solution.

A preferred technical solution is as follows: in S3, chromatographic parameters were as follows: the sample mass concentration is 40 mg/mL; the injection volume was 200 μL; the eluent is 0.01 M of hydrochloric acid buffer solution at a flow rate of 0.5 mL/min, the primary UV ultraviolet detection wavelength is 214 nm, and the secondary UV ultraviolet detection wavelength is 250 nm.

A preferred technical solution is as follows: in S3, further purification is performed by ion exchange chromatography, and specific detection conditions are as follows: the sample mass concentration was 10 mg/mL; the injection volume is 2 mL; a chromatographic column is the DEAE anion column with a mobile phase A of 20 mM Tris-HCl buffer solution and a mobile phase B of 20 mM Tris-HCl buffer solution+ 1M NaCl; the gradient elution: the first gradient: 100% of the mobile phase A, 0% of the mobile phase B, and 60 mL of the elution volume; the second gradient: 90% of the mobile phase A, 10% of the mobile phase B, and 60 mL of the elution volume; the third gradient: 100% of the mobile phase A, 0% of the mobile phase B, and 40 mL of the elution volume; the elution rate is 5 mL/min, the primary UV ultraviolet detection wavelength is 214 nm, and the secondary UV ultraviolet detection wavelength is 250 nm; and pH values of the mobile phase A and the mobile phase B are both 9.0.

A preferred technical solution is as follows: chromatographic conditions for the UPLC-Triple-TOF/MS are as follows: the chromatographic column is Agilent Eclipse Plus-C18; the mobile phase A is ultrapure water containing 0.1% of trifluoroacetic acid; the mobile phase B is acetonitrile containing 0.1% of trifluoroacetic acid; and the linear gradient elution is as follows:

100% of the mobile phase A, and 0% of the mobile phase B 0-1 min;
100%-70% of the mobile phase A, and 0%-30% of the mobile phase B 1-10 min;
70%-0% of the mobile phase A, and 30%-100% of the mobile phase B 10-15 min;
0% of the mobile phase A and 100%-0% of the mobile phase B 15-18 min;
0%-100% of the mobile phase A, and 100%-0% of the mobile phase B 18-22 min;
100% of the mobile phase A and 100%-0% of the mobile phase B 22-25 min A preferred technical solution is as follows: the Sephadex G-15 gel filtration column has an inner column of 3.0 cm and a column length of 200 cm; the DEAE anion column has an inner diameter of 16 mm and a column length of 25 mm; and the C18 chromatographic column has an inner diameter of 4.6 mm, a column length of 150 mm and a particle size of 3.5 μm.

Compared with the prior art, the present disclosure has the following advantages due to the application of the above technical solutions:

1. The salty taste enhancing peptide of the present disclosure features small molecular weight, strong salty taste enhancing effect and simple sequences, and is easy to separate, purify and synthesize, therefore, the salty taste enhancing peptide can be applied to the fields of food, health products, medicine and biology, and expected to replace salt substitute products currently available on the market.
2. The present disclosure selects the famous Chinese Jinhua dry-cured ham, crude peptides are concentrated by dialysis, the Sephadex G-15 gel filtration column and the DEAE anion column are used to make purification, components with the optimal salty taste enhancing effect are screened out, and the amino acid sequence is identified as Asp-Leu (DL) by the liquid chromatography-mass spectrometry.
3. Components with the optimal salty taste enhancing effect can be accurately screened out through the sensory evaluation and analysis of electronic tongue-assisted evaluation, and it can be concluded that the salty taste enhancing peptide sequences also have umami synergistic effect through electronic tongue-assisted evaluation.

BRIEF DESCRIPTION OF THE DRAWINGS

FIG. 9 is a sensory evaluation table of ion-exchange purified components.

DETAILED DESCRIPTIONS OF THE EMBODIMENTS

The implementation of the present disclosure will be illustrated below in conjunction with specific embodiments. Those skilled in the art can easily understand other advantages and effects of the present disclosure from the content disclosed in this specification.

Figures 1, 2:
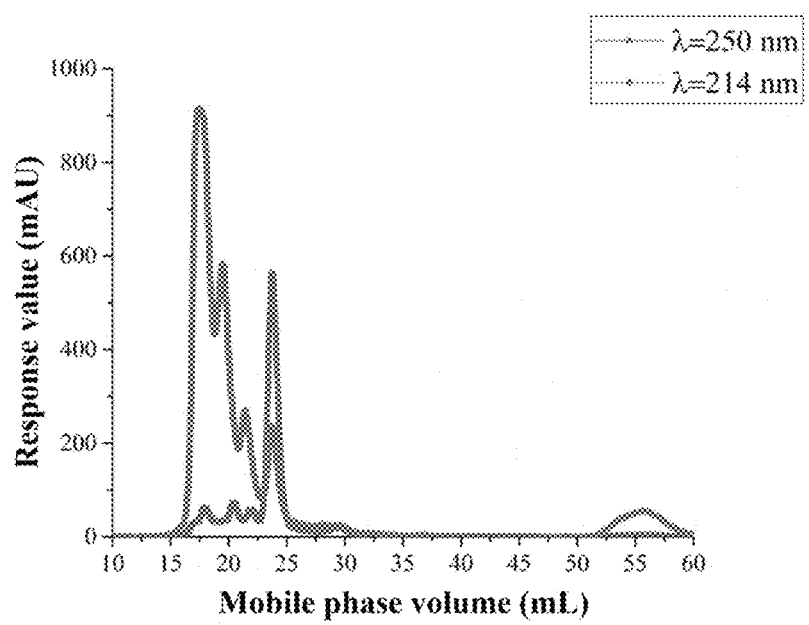
FIG. 1 is a chromatogram of Sephadex G-15 gel.
FIG. 2 is a sensory evaluation of gel-purified components.
Figure 3:
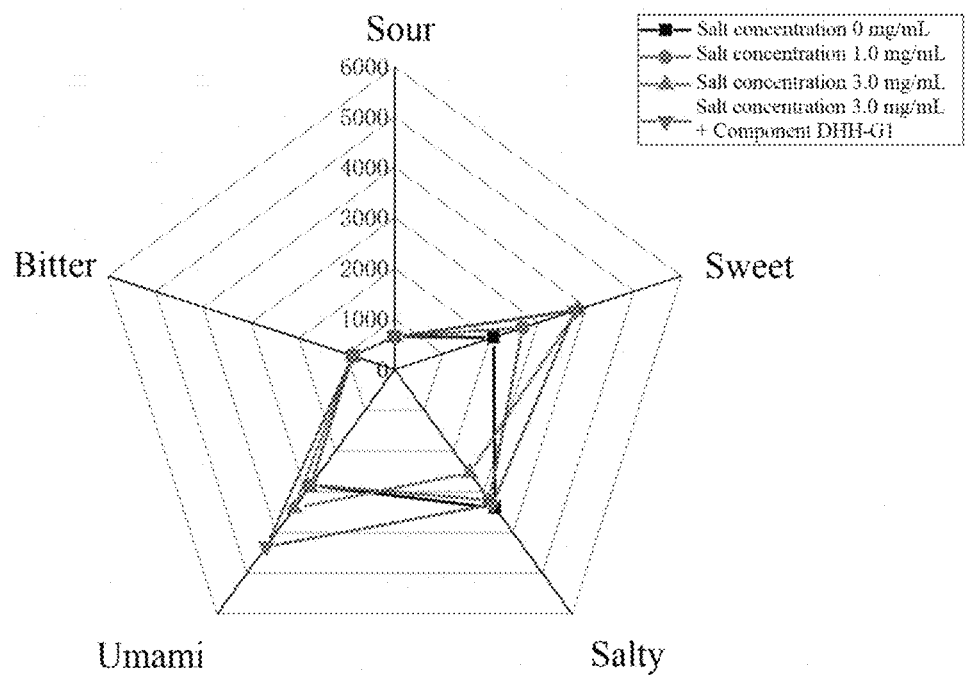
FIG. 3 is a radar chart of electronic tongue flavor analysis of gel-purified component 1.
Figure 4:
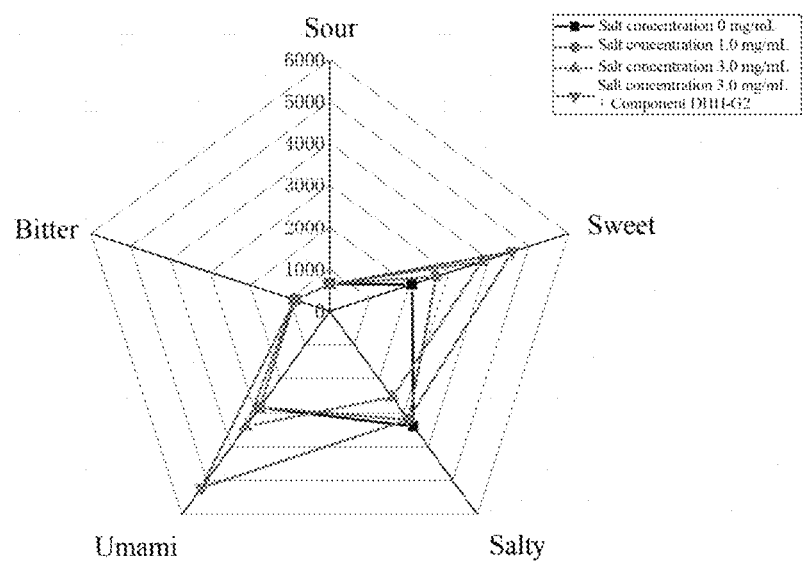
FIG. 4 is a radar chart of electronic tongue flavor analysis of gel-purified component 2.
Figure 5:
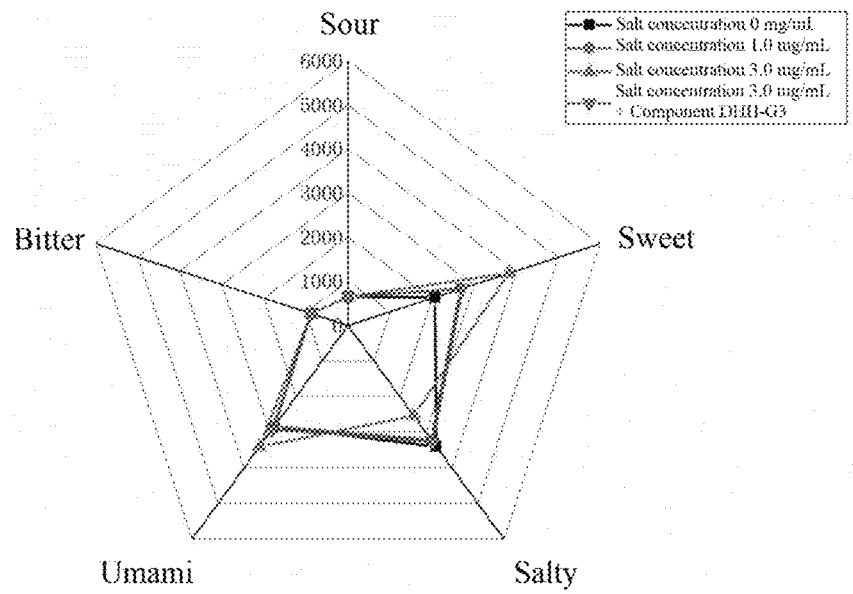
FIG. 5 is a radar chart of electronic tongue flavor analysis of gel-purified component 3.
Figure 6:
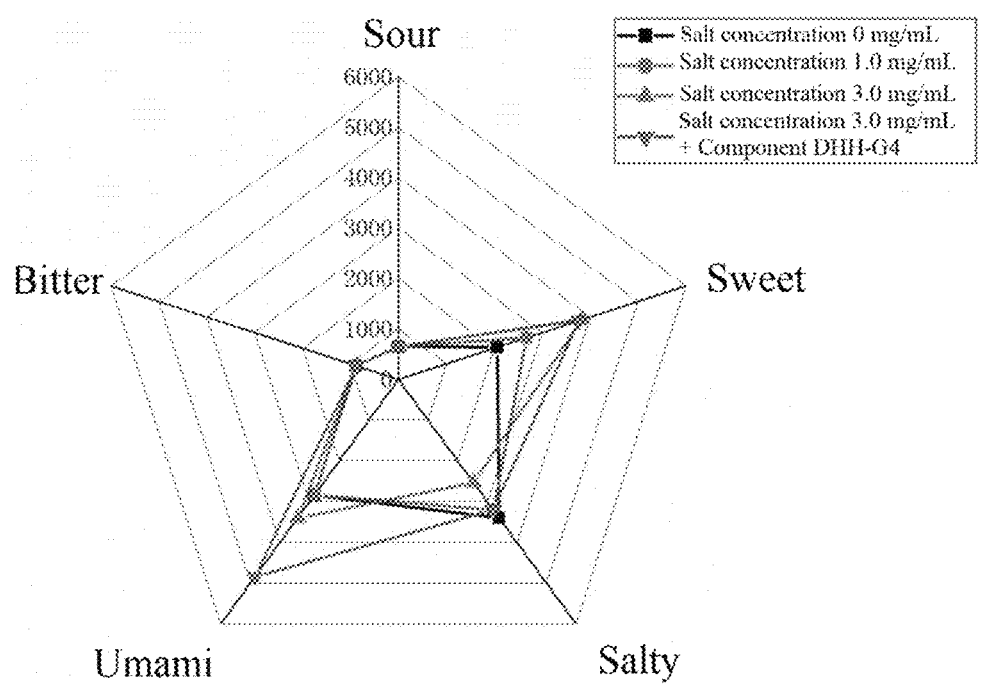
FIG. 6 is a radar chart of electronic tongue flavor analysis of gel-purified component 4.
Figure 7:
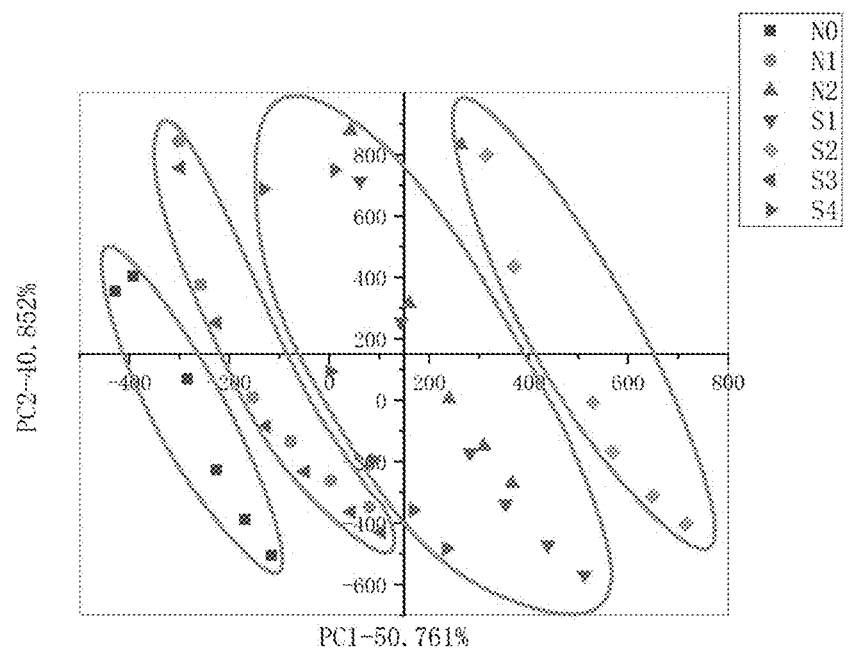
FIG. 7 is a PCA plot of gel-purified components.
Figure 8:
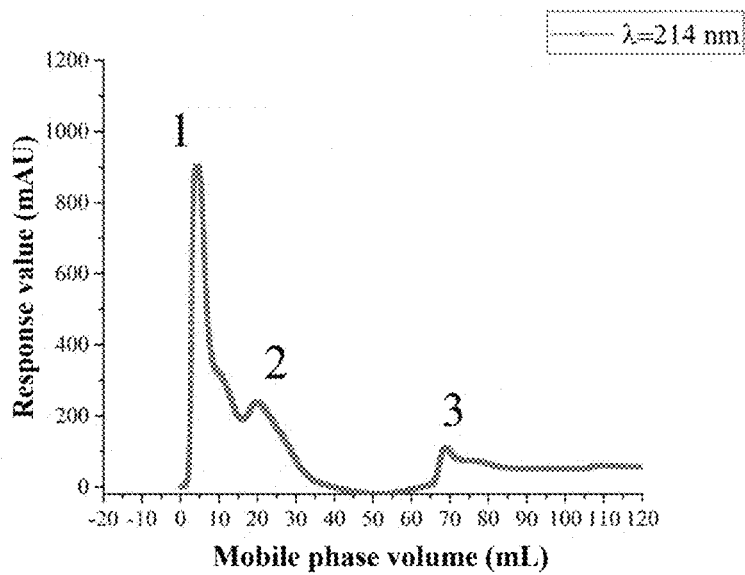
FIG. 8 is an ion exchange chromatogram.
Figure 10:
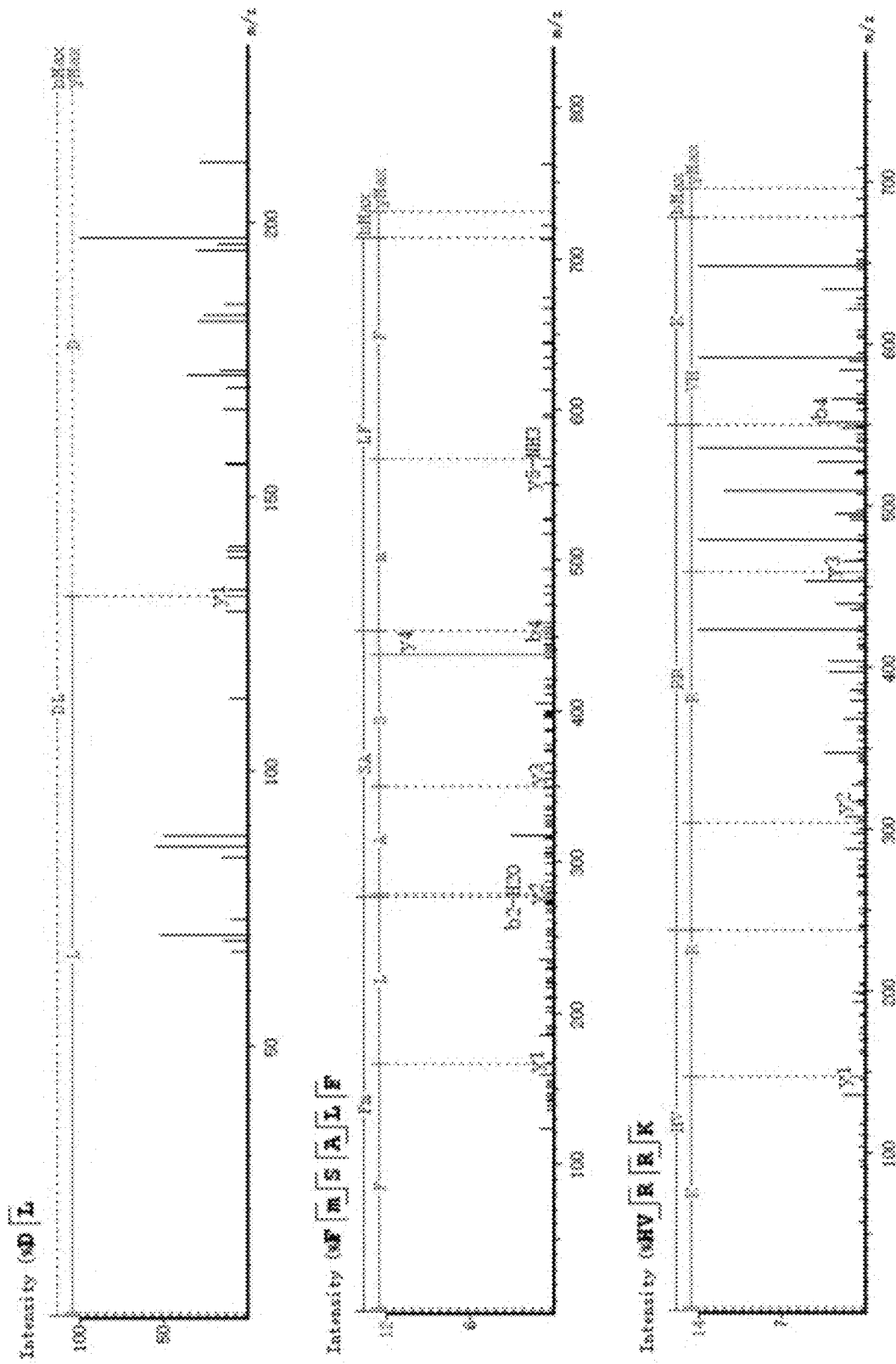
FIG. 10 is a secondary mass spectrum of the optimal salty taste enhancing component.

With reference to FIGS. 1-10, it should be noted that the structures, scales, sizes, and the like shown in the drawings attached to the specification are only used to match the content disclosed in the specification and for those skilled in the art to understand and read, instead of being used to limit the limitations for implementing the present disclosure, and they are thus not technically substantial, nor are they any structural modification, scale relation change, or size adjustment. The following examples are provided for a better understanding of the present disclosure, instead of limiting the present disclosure. Experimental methods in the following examples are conventional unless otherwise specified. Experimental materials used in the following examples were all purchased from conventional biochemical reagent stores unless otherwise specified.

Example 1: A Salty Taste Enhancing Peptide Derived from Dry-Cured Ham and a Preparation Method Thereof The salty taste enhancing peptide of the present disclosure specifically corresponds to Component 1 in FIG. 1 and Peak 1 in FIG. 5.

A salty taste enhancing peptide derived from dry-cured ham, where the amino acid sequence of the salty taste enhancing peptide is: Asp-Leu (DL).

The salty taste enhancing peptide has strong salty taste enhancing effect and can be applied to preparing salt substitutes or salty taste enhancer, and health food.

S1. Preparation of Ham-Derived Extract

The hind leg meat of Chinese Jinhua Ham, a dry-cured ham, was processed into powder. 50 g of the powder sample was weighed and dissolved in 150 mL of 0.01 mol/L hydrochloric acid buffer solution, homogenized 4 times at 16,000 r/min for 10 s each time, and then centrifuged at a rotating speed of 12,000 r/min at −4° C. for 20 min, the supernatant was taken and subject to suction filtration with a 0.45 μm filter membrane, and ham-derived extract was obtained after suction filtration.

S2. Dialysis and Preparation of the Ham-Derived Extract

The ham-derived extract obtained above was placed into a dialysis bag of less than 3,000 Da and dialyzed for 24 h at −4° C., the obtained dialysate was then concentrated by rotary steaming at 65° C. to obtain a concentrated solution, and the concentrated solution was frozen to dry in a freeze dryer to obtain crude polypeptides.

S3. Separation and Purification of the Crude Polypeptides

The crude polypeptides obtained in S2 were dissolved in pure water, filtered by 0.22 μm of aqueous phase membrane, and then loaded onto a Sephadex G-15 gel filtration column (3.0×200 cm) for purification at 25° C. Specific chromatographic parameters: the sample mass concentration was 40 mg/mL; the injection volume was 200 μL; the eluent was 0.01 M of hydrochloric acid buffer solution at a flow rate of 0.5 mL/min, the primary UV ultraviolet detection wavelength was 214 nm, and the secondary UV ultraviolet detection wavelength was 250 nm. All purified components were subject to a sensory evaluation according to their respective chromatographic peaks. Components with the optimal salty taste enhancing effect were screened out through the sensory evaluation and analysis of electronic tongue-assisted sensory characteristics.

Components with the optimal salty taste enhancing effect obtained from gel separation were further purified by ion exchange chromatography. Specific detection conditions: the sample mass concentration was 10 mg/mL; the injection volume was 2 mL; a chromatographic column was the DEAE anion column (16×25 mm) with a mobile phase A of 20 mM Tris-HCl buffer solution (pH=9.0) and a mobile phase B of 20 mM Tris-HCl buffer solution+1M NaCl (pH=9.0); the gradient elution: the first gradient: 100% of the mobile phase A, 0% of the mobile phase B, and 60 mL of the elution volume; the second gradient: 90% of the mobile phase A, 10% of the mobile phase B, and 60 mL of the elution volume; the third gradient: 100/6 of the mobile phase A, 0% of the mobile phase B, and 40 mL of the elution volume; the elution rate was 5 mL/min, the primary UV ultraviolet detection wavelength was 214 nm, and the secondary UV ultraviolet detection wavelength was 250 nm. All purified components were subject to a sensory evaluation according to their respective chromatographic peaks. Components with the optimal salty taste enhancing effect were screened out through the sensory evaluation and analysis of electronic tongue-assisted sensory characteristics.

S4. Amino Acid Sequence Test of the Salty Taste Enhancing Peptide

Components with the optimal salty taste enhancing effect obtained in S3 were subject to an ultra-high-performance liquid chromatography-triple quadrupole time-of-flight mass spectrum ("UPLC-Triple-TOF/MS" for short) to identify the sequence of the salty taste enhancing peptide. Chromatographic conditions were as follows: the chromatographic column was Agilent Eclipse Plus-C18; the mobile phase A was ultrapure water containing 0.1% of trifluoroacetic acid; the mobile phase B was acetonitrile containing 0.1% of trifluoroacetic acid; and the linear gradient elution: 100% of the mobile phase A, 0% of the mobile phase B (0-1 min); 100%-70% of the mobile phase A, 0%-30% of the mobile phase B (1-10 min); 70%-0% of the mobile phase A, 30%-100% of the mobile phase B (10-15 min); 0% of the mobile phase A, 100% of the mobile phase B (15-18 min); 0%-100% of the mobile phase A, 100%-0% of the mobile phase B (18-22 min); 100% of the mobile phase A and 0% of the mobile phase B (22-25 min). The liquid chromatography-mass spectrometry was used to determine the amino acid sequences as Asp-Leu(DL); and Phe-Met-Ser-Ala-Leu-Phe (FMSALF), as shown in SEQ ID NO: 1; His-Val-Arg-Arg-Lys(HVRRK), as shown in SEQ ID NO: 2; where Asp-Leu (DL) can be matched in silico.

All steps of the method for separation and purification of a salty taste enhancing peptide derived from dry-cured ham in the example are the same as those in Example 2, with the following differences:
(1) the mobile phase for gel filtration in S3 was 0.01 M of Tris-HCl buffer solution at a flow rate of 0.4 mL/min; and
(2) chromatographic conditions for ion exchange in S3: the gradient elution: the first gradient: 100% of the mobile phase A, 0% of the mobile phase B, and 120 mL of the elution volume; the second gradient: 95% of the mobile phase A, 5% of the mobile phase B, and 40 mL of the elution volume; the third gradient: 90% of the mobile phase A, 10% of the mobile phase B, and 40 mL of the elution volume.

Example 2: A Preparation Method of a Salty Taste Enhancing Peptide Derived from Dry-Cured Ham All steps of the method for separation and purification of a salty taste enhancing peptide derived from dry-cured ham in the example are the same as those in Example 2, with the following differences:
(1) the mobile phase for gel filtration in S3 was ultrapure water at a flow rate of 0.4 mL/min;
(2) the detection wavelength in gel filtration in S3 was 220 nm; and
(3) chromatographic conditions for ion exchange in S3: the mobile phase A was ultrapure water, and the mobile phase B was 2M NaCl.

Example 3: A Salty Taste Enhancing Peptide Derived from Dry-Cured Ham and a Preparation Method Thereof The preparation method of a salty taste enhancing peptide derived from dry-cured ham includes the following steps:

S1. Preparation of Ham-Derived Extract

The ham was processed to obtain power, the power was dispersed in a hydrochloric acid buffer solution, homogenized and then centrifuged, the supernatant was then taken and subject to suction filtration, and ham-derived extract was obtained after suction filtration;

S2. Dialysis and Preparation of the Ham-Derived Extract

The ham-derived extract obtained above was dialyzed to obtain dialysate, the dialysate was then concentrated to obtain a concentrated solution, the concentrated solution was frozen to dry to obtain crude polypeptides.

S3. Separation and Purification of the Crude Polypeptides

The crude polypeptides were dissolved in pure water and filtered, the filtered solution was loaded onto a Sephadex G-15 gel filtration column for purification, purified peptides were obtained, further purification was performed by ion exchange chromatography, a sensory evaluation was conducted on all purified components according to their respective chromatographic peaks, and components with the optimal salty taste enhancing effect were screened out through the sensory evaluation and analysis of electronic tongue-assisted sensory characteristics.

S4. Amino Acid Sequence Test of the Salty Taste Enhancing Peptide

Components with the optimal salty taste enhancing effect obtained in S3 were subject to a UPLC-Triple-TOF/MS to identify sequences of the salty taste enhancing peptide, and three amino acid sequences were determined as Asp-Leu; Phe-Met-Ser-Ala-Leu-Phe, as shown in SEQ ID NO: 1; and His-Val-Arg-Arg-Lys, as shown in SEQ ID NO: 2.

A preferred embodiment was as follows: in S1, the concentration of the hydrochloric acid buffer solution was 0.01 mol/L, and the ratio of the powder to the hydrochloric acid buffer solution was 50 g: 100 mL; homogenate was performed 3 times at 15,000 r/min for 8 s each time; centrifugation was performed at a rotating speed of 10,000 r/min at −3° C. for 15 min; and the supernatant was subject to suction filtration with a 0.45 μm filter membrane.

A preferred embodiment was as follows: in S2, the ham-derived extract was placed into a dialysis bag of less than 3,000 Da and dialyzed for 20 h at −3° C., the obtained dialysate was evaporated by rotary steaming at 60° C. to obtain a concentrated solution.

A preferred embodiment was as follows: in S3, chromatographic parameters were as follows: the sample mass concentration was 40 mg/mL; the injection volume was 200 μL; the eluent was 0.01 M of hydrochloric acid buffer solution at a flow rate of 0.5 mL/min, the primary UV ultraviolet detection wavelength was 214 nm, and the secondary UV ultraviolet detection wavelength was 250 nm.

A preferred embodiment was as follows: in S3, further purification was performed by ion exchange chromatography, and specific detection conditions were as follows: the sample mass concentration was 10 mg/mL; the injection volume was 2 mL; a chromatographic column was the DEAE anion column with a mobile phase A of 20 mM Tris-HCl buffer solution and a mobile phase B of 20 mM Tris-HCl buffer solution+1M NaCl; the gradient elution: the first gradient: 100% of the mobile phase A, 0% of the mobile phase B, and 60 mL of the elution volume; the second gradient: 90% of the mobile phase A, 10% of the mobile phase B, and 60 mL of the elution volume; the third gradient: 100% of the mobile phase A, 0% of the mobile phase B, and 40 mL of the elution volume; the elution rate was 5 mL/min, the primary UV ultraviolet detection wavelength was 214 nm, and the secondary UV ultraviolet detection wavelength was 250 nm; and pH values of the mobile phase A and the mobile phase B were both 9.0.

A preferred embodiment was as follows: chromatographic conditions for the UPLC-Triple-TOF/MS were as follows: the chromatographic column was Agilent Eclipse Plus-C18; the mobile phase A was ultrapure water containing 0.1% of trifluoroacetic acid; the mobile phase B was acetonitrile containing 0.1% of trifluoroacetic acid; and the linear gradient elution was as follows:

100% of the mobile phase A, and 0% of the mobile phase B 0-1 min;

100%-70% of the mobile phase A, and 0%-30% of the mobile phase B 1-10 min;

70%-0% of the mobile phase A, and 30%-100% of the mobile phase B 10-15 min;

0% of the mobile phase A and 100%-0% of the mobile phase B 15-18 min;

0%-100% of the mobile phase A, and 100%-0% of the mobile phase B 18-22 min;

100% of the mobile phase A and 100%-0% of the mobile phase B 22-25 min

A preferred embodiment was as follows: the Sephadex G-15 gel filtration column had an inner column of 3.0 cm and a column length of 200 cm, the DEAE anion column had an inner diameter of 16 mm and a column length of 25 mm; and the C18 chromatographic column had an inner diameter of 4.6 mm, a column length of 150 mm and a particle size of 3.5 μm.

Example 4: A Salty Taste Enhancing Peptide Derived from Dry-Cured Ham and a Preparation Method Thereof The preparation method of a salty taste enhancing peptide derived from dry-cured ham includes the following steps:

S1. Preparation of Ham-Derived Extract

The ham was processed to obtain power, the power was dispersed in a hydrochloric acid buffer solution, homogenized and then centrifuged, the supernatant was taken and subject to suction filtration, and ham-derived extract was obtained after suction filtration;

S2. Dialysis and Preparation of the Ham-Derived Extract

The ham-derived extract obtained above was dialyzed to obtain dialysate, the dialysate was then concentrated to obtain a concentrated solution, the concentrated solution was frozen to dry to obtain crude polypeptides.

S3. Separation and Purification of the Crude Polypeptides

The crude polypeptides were dissolved in pure water and filtered, the filtered solution was loaded onto a Sephadex G-15 gel filtration column for purification, purified peptides were obtained, further purification was performed by ion exchange chromatography, a sensory evaluation was conducted on all purified components according to their respective chromatographic peaks, and components with the optimal salty taste enhancing effect were screened out through the sensory evaluation and analysis of electronic tongue-assisted sensory characteristics.

S4. Amino Acid Sequence Test of the Salty Taste Enhancing Peptide

Components with the optimal salty taste enhancing effect obtained in S3 were subject to a UPLC-Triple-TOF/MS to identify sequences of the salty taste enhancing peptide, and three amino acid sequences were determined as Asp-Leu; Phe-Met-Ser-Ala-Leu-Phe, as shown in SEQ ID NO: 1; and His-Val-Arg-Arg-Lys, as shown in SEQ ID NO: 2.

A preferred embodiment was as follows: in S1, the concentration of the hydrochloric acid buffer solution was 0.01 mol/L, and the ratio of the powder to the hydrochloric acid buffer solution was 50 g: 200 mL; homogenate was performed 5 times at 18,000 r/min for 12 s each time; centrifugation was performed at a rotating speed of 14,000 r/min at −5° C. for 25 min; and the supernatant was subject to suction filtration with a 0.45 μm filter membrane.

A preferred embodiment was as follows: in S2, the ham-derived extract was placed into a dialysis bag of less than 3,000 Da and dialyzed for 28 h at −5° C., the obtained dialysate was evaporated by rotary steaming at 70° C. to obtain a concentrated solution.

A preferred embodiment was as follows: in S3, chromatographic parameters were as follows: the sample mass concentration was 40 mg/mL; the injection volume was 200 μL; the eluent was 0.01 M of hydrochloric acid buffer solution at a flow rate of 0.5 mL/min, the primary UV ultraviolet detection wavelength was 214 nm, and the secondary UV ultraviolet detection wavelength was 250 nm.

A preferred embodiment was as follows: in S3, further purification was performed by ion exchange chromatography, and specific detection conditions were as follows: the sample mass concentration was 10 mg/mL; the injection volume was 2 mL; a chromatographic column was the DEAE anion column with a mobile phase A of 20 mM Tris-HCl buffer solution and a mobile phase B of 20 mM Tris-HCl buffer solution+1M NaCl; the gradient elution: the first gradient: 100% of the mobile phase A, 0% of the mobile phase B, and 60 mL of the elution volume; the second gradient: 90% of the mobile phase A, 10% of the mobile phase B, and 60 mL of the elution volume; the third gradient: 100% of the mobile phase A, 0% of the mobile phase B, and 40 mL of the elution volume; the elution rate was 5 mL/min, the primary UV ultraviolet detection wavelength was 214 nm, and the secondary UV ultraviolet detection wavelength was 250 nm; and pH values of the mobile phase A and the mobile phase B were both 9.0.

A preferred embodiment was as follows: chromatographic conditions for the UPLC-Triple-TOF/MS were as follows: the chromatographic column was Agilent Eclipse Plus-C18; the mobile phase A was ultrapure water containing 0.1% of trifluoroacetic acid; the mobile phase B was acetonitrile containing 0.1% of trifluoroacetic acid, and the linear gradient elution was as follows:

100% of the mobile phase A, and 0% of the mobile phase B 0-1 min;
100%-70% of the mobile phase A, and 0%-30% of the mobile phase B 1-10 min;
70%-0% of the mobile phase A, and 30%-100% of the mobile phase B 10-15 min;
0% of the mobile phase A and 100%-0% of the mobile phase B 15-18 min;
0%-100% of the mobile phase A, and 100%-0% of the mobile phase B 18-22 min;
100% of the mobile phase A and 100%-0% of the mobile phase B 22-25 min A preferred embodiment was as follows: the Sephadex G-15 gel filtration column had an inner column of 3.0 cm and a column length of 200 cm; the DEAE anion column had an inner diameter of 16 mm and a column length of 25 mm; and the C18 chromatographic column had an inner diameter of 4.6 mm, a column length of 150 mm and a particle size of 3.5 μm.

The aforesaid embodiments are only intended to give explanation of preferred embodiments of the present disclosure, but are not intended to limit the present disclosure in any form. Therefore, any modifications or alterations made in relation to the present disclosure under the same spirit of the present disclosure shall fall under the intended protection scope of the present disclosure.

SEQUENCE LISTING

```
Sequence total quantity: 2
SEQ ID NO: 1           moltype = AA  length = 6
FEATURE                Location/Qualifiers
REGION                 1..6
                       note = The sequence is synthetized.
source                 1..6
                       mol_type = protein
                       organism = synthetic construct
SEQUENCE: 1
FMSALF                                                                  6

SEQ ID NO: 2           moltype = AA  length = 5
FEATURE                Location/Qualifiers
REGION                 1..5
                       note = The sequence is synthetized.
source                 1..5
                       mol_type = protein
                       organism = synthetic construct
SEQUENCE: 2
HVRRK                                                                   5
```

What is claimed is:

1. A preparation method of salty taste enhancing peptides derived from a dry-cured ham, wherein the salty taste enhancing peptides comprise a first component having an amino acid sequence represented by Phe-Met-Ser-Ala-Leu-Phe (SEQ ID NO:1), and a second component having an amino acid sequence represented by His-Val-Arg-Arg-Lys (SEQ ID NO:2), the method comprising the following steps:

S1. preparing a ham-derived extract, including:
processing the dry-cured ham to obtain a powder;
dispersing the powder in a hydrochloric acid buffer solution to obtain a first resulting solution;
homogenizing the first resulting solution to obtain a homogenized solution;
centrifuging the homogenized solution to obtain a supernatant; and
taking the supernatant and performing a suction filtration on the supernatant to obtain the ham-derived extract;

S2. preparing crude polypeptides, including:
dialyzing the ham-derived extract to obtain a dialysate;
concentrating the dialysate to obtain a concentrated solution; and
freezing and drying the concentrated solution to obtain the crude polypeptides; and S3. preparing the salty taste enhancing peptides by separation and purification of the crude polypeptides, including:
dissolving the crude polypeptides in pure water to obtain a second resulting solution, and filtrating the second resulting solution to obtain a filtered solution;
loading the filtered solution onto a gel filtration column for a first purification to obtain first purified peptides;
performing a second purification on the first purified peptides by an ion exchange chromatography to obtain second purified peptides;
carrying out a sensory evaluation on purified components of the second purified peptides according to respective chromatographic peaks of the purified components, and screening out a component having an amino acid sequence represented by Phe-Met-Ser-Ala-Leu-Phe (SEQ ID NO:1) as the first component, and a component having an amino acid sequence represented by His-Val-Arg-Arg-Lys (SEQ ID NO:2) as the second component from the purified components through the sensory evaluation and an analysis of an electronic tongue-assisted sensory characteristic, wherein the sequences of screened components are determined by performing an ultra-high-performance liquid chromatography-triple quadrupole time-of-flight mass spectrum (UPLC-Triple-TOF/MS) on the screened components.

2. The preparation method of the salty taste enhancing peptides derived from the dry-cured ham according to claim 1, wherein in S1, a concentration of the hydrochloric acid buffer solution is 0.01 mol/L, and a ratio of the powder to the hydrochloric acid buffer solution is 50 g:(100-200) mL; the homogenizing is performed 3-5 times at 15,000-18,000 r/min for 8-12 s each time; the centrifuging is performed at a rotating speed of 10,000-14,000 r/min at −3--5° C. for 15-25 min; and the supernatant is subject to the suction filtration with a filter membrane with a pore size of 0.45 μm.

3. The preparation method of the salty taste enhancing peptides derived from the dry-cured ham according to claim 1, wherein in S2, the ham-derived extract is placed into a dialysis bag of less than 3,000 Da and dialyzed for 20-28 h at −3--5° C., the dialysate is concentrated by a rotary steaming at 60-70° C. to obtain the concentrated solution.

4. The preparation method of the salty taste enhancing peptides derived from the dry-cured ham according to claim 1, wherein in S3, chromatographic parameters of the gel filtration column are as follows: a sample mass concentration is 40 mg/mL; an injection volume is 200 μL; an eluent is 0.01 M of the hydrochloric acid buffer solution at a flow rate of 0.5 mL/min, a primary UV ultraviolet detection wavelength is 214 nm, and a secondary UV ultraviolet detection wavelength is 250 nm.

5. The preparation method of the salty taste enhancing peptides derived from the dry-cured ham according to claim 1, wherein in S3, detection conditions of the ion exchange chromatography are as follows: a sample mass concentration is 10 mg/mL; an injection volume is 2 mL; a chromatographic column of the ion exchange chromatography is a DEAF anion column with a first mobile phase of 20 mM Tris-HCl buffer solution and a second mobile phase of 20 mM Tris-HCl buffer solution+1M NaCl; a gradient elution is as follows: a first gradient is conducted with 100% of the first mobile phase, 0% of the second mobile phase, and 60 mL of an elution volume; a second gradient is conducted with 90% of the first mobile phase, 10% of the second mobile phase, and 60 mL of the elution volume; a third gradient is conducted with 100% of the first mobile phase, 0% of the second mobile phase, and 40 mL of the elution volume; an elution rate of the gradient elution is 5 mL/min, a primary UV ultraviolet detection wavelength is 214 nm, and a secondary UV ultraviolet detection wavelength is 250 nm; and a pH value of the first mobile phase and a pH value of the second mobile phase are 9.0.

6. The preparation method of the salty taste enhancing peptides derived from the dry-cured ham according to claim 5, wherein chromatographic conditions of the UPLC-Triple-TOF/MS are as follows: a third mobile phase is an ultrapure water containing trifluoroacetic acid at a volume ratio of 0.1%; fourth mobile phase is an acetonitrile containing trifluoroacetic acid at a volume ratio of 0.1%; and a linear gradient elution is as follows:
using 100% of the third mobile phase and 0% of the fourth mobile phase to elute for 0-1 min;
using 100%-70% of the third mobile phase and 0%-30% of the fourth mobile phase to elute for 1-10 min;
using 70%-0% of the third mobile phase and 30%-100% of the fourth mobile phase to elute for 10-15 min;
using 0% of the third mobile phase and 100% of the fourth mobile phase to elute for 15-18 min;
using 0%-100% of the third mobile phase and 100%-0% of the fourth mobile phase to elute for 18-22 min; and
using 100% of the third mobile phase and 0% of the fourth mobile phase to elute for 22-25 min.

7. The preparation method of the salty taste enhancing peptides derived from the dry-cured ham according to claim 6, wherein the gel filtration column has an inner column of 3.0 cm and a column length of 200 cm; the DEAE anion column has an inner diameter of 16 mm and a column length of 25 mm; and a chromatographic column of the UPLC-Triple-TOF/MS has an inner diameter of 4.6 mm, a column length of 150 mm, and a particle size of 3.5 μm.

* * * * *